United States Patent [19]

Glenn et al.

[11] Patent Number: 5,076,933
[45] Date of Patent: Dec. 31, 1991

[54] PROCESS AND APPARATUS FOR REMOVAL OF DNA AND VIRUSES

[75] Inventors: Stephan D. Glenn, Davie; Edward O'Connell, Miami; Paulette Smariga; Gregory Butchko, both of Miami Lakes, all of Fla.

[73] Assignee: Coulter Corporation, Hialeah, Fla.

[21] Appl. No.: 546,011

[22] Filed: Jun. 29, 1990

[51] Int. Cl.$^5$ ............... B01D 25/00; B01D 63/08; B01D 71/10

[52] U.S. Cl. ............... 210/641; 210/651; 210/655; 210/32.64; 210/335; 210/446; 210/500.29; 210/506; 422/1; 422/101; 435/311; 935/19

[58] Field of Search .............. 210/641, 652, 653, 655, 210/321.64, 321.84, 335, 446, 500.29, 506, 507, 508; 422/1, 101; 435/371; 935/19

[56] References Cited

U.S. PATENT DOCUMENTS

| | | | |
|---|---|---|---|
| 3,676,335 | 7/1972 | Lacey et al. | 210/641 |
| 4,168,300 | 9/1979 | Andersson et al. | 210/679 X |
| 4,420,398 | 12/1983 | Castino | 210/641 |
| 4,431,545 | 2/1984 | Pall et al. | 210/641 |
| 4,473,474 | 9/1984 | Ostreicher et al. | 210/650 X |
| 4,869,826 | 9/1989 | Wang et al. | 210/641 |
| 4,935,142 | 6/1990 | Sternberg | 210/321.84 X |

FOREIGN PATENT DOCUMENTS 57-197085 12/1982 Japan ................... 210/641

OTHER PUBLICATIONS

Schleicher & Schuell product Information Sheet No. 364.
G. Sofer, "Chromatographic Removal of Pyrogens", Biotechnology, Dec., 1984, p. 1035 et seq.
Gerba et al., "Applied & Environmental Microbioogy": 50:1375-1377 (1985).
S. Minobe et al., J. Chromatography, 248:401-408 (1982).

*Primary Examiner*—W. Gary Jones
*Attorney, Agent, or Firm*—Myron C. Cass

[57] ABSTRACT

A single filtration device containing coated filter membranes and absolute pore filters is provided in which the membranes and absolute pore filters are present in two sections of the filter device. The filter device will remove viruses, as modeled by type-C Xenotropic retrovirus, with an efficiency of at least $4.6 \times 10^5$; remove DNA from levels of 10 μg/sample to levels below 10 picograms per 500 mg sample of monoclonal antibody; and will remove at least 97% of some bacterial endotoxins.

26 Claims, 2 Drawing Sheets

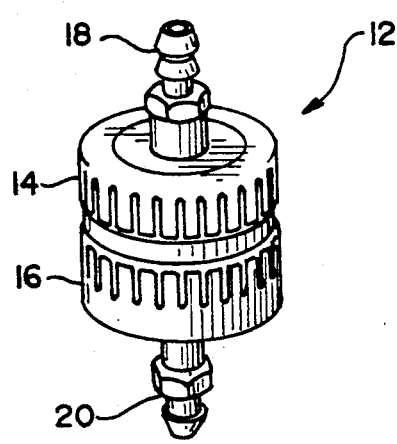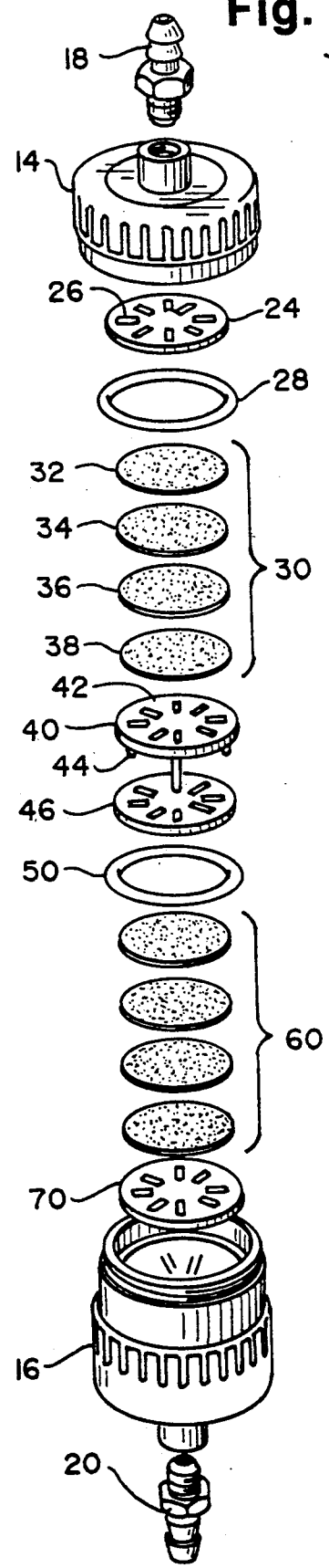

PROCESS AND APPARATUS FOR REMOVAL OF DNA AND VIRUSES

FIELD OF THE INVENTION

The present invention relates to a process for removing DNA and viruses from physiological fluids and medicant solutions administered to humans and animals, and an apparatus for performing said process. More particularly, the invention is especially effective for removing DNA, viruses and endotoxins from biological pharmaceutical solutions and biological media, for example, DNA, viruses and endotoxins from a monoclonal antibody solution, buffer solutions or a solution of bovine serum albumin.

BACKGROUND OF THE INVENTION

One objective in the preparation of pharmaceutical solutions, buffer solutions, life support solutions, saline solutions and other such solutions which are to be administered to animals and humans is that they be as free as possible from substances which might cause an adverse reaction in the host. While a goal of zero contamination by substances such as DNA, viruses and endotoxins is always sought, in actual practice very minute amounts of such substances are sometimes present. The Food and Drug Administration (FDA) has sets standards for such substances which cannot be exceeded. Manufacturers, ever mindful that a batch of medicant may be rejected if the level of such substances is too high, continually seek new methods to ensure that their products do not exceed FDA standards. Consequently, in all phases of the manufacturing process, manufacturers seek to ensure the purity of the reagents used in the manufacture as well as the final product. Many of the medicants and other products mentioned above are either sold as aqueous solutions or are manufactured in aqueous medium. Consequently, the manufacturers seek to ensure that the water they use is free of DNA, viruses and endotoxins.

One technology that such manufacturers often use is ultrafiltration. U.S. Pat. Nos. 4,431,545 to Pall et al, 4,816,162 to Rosskopf et al, and 4,420,398 to Castino, describe dual-module filtration to remove pathological and/or toxic substances from various fluids including water, blood and plasma. U.S. Pat. No. 4,431,545 utilizes dual filters, one of which has a negative zeta potential and one of which has a positive zeta potential, to filter out positively and negatively charged particles. Neutral particles are removed in accordance with the pore size ratings of the filters which are 0.01 microns or larger as disclosed. U.S. Pat. No. 4,816,162 describes an apparatus that removes immunoglogins, albumin and lipoproteins from blood, blood plasma or serum, but does not describe the removal of DNA or viruses. The filter in this patent is designed for use in circulating and purifying blood during surgery. U.S. Pat. No. 4,420,398 describes a filtration method for separating cell produced antiviral substances, including monoclonal antibodies, from the reaction "broth" in which they are produced. This patent does not indicate whether the resulting species are free of viruses, endotoxins and DNA which may cause a reaction within a patient.

It is known in the prior art that multiple filtration with a 0.04 micron absolute pore size filter will remove viruses of 0.075 micron size, but not smaller viruses. For example, filtration of calf serum containing MS 2 phage (0.024 micron) through 0.04 micron will not remove the virus. In those circumstances where virus can be removed, removal rate is typically 99.9 to 99.99% per filter pass. For example, using a 0.04 micron filter, applicants removed all detectable Reovirus (0.075 micron) from a sample containing $10^8$ virus particles per milliliter sample. An article published in the April, 1990 issue of Genetic Engineering News (page 6) commented on the Food and Drug Administration's (FDA) increasing emphasis on viral removal protocols with regard to the preparation of biological pharmaceuticals and the efforts being made by filter manufacturers to achieve higher degrees of virus removal.

Another contaminant which can be present in biological pharmaceuticals such as monoclonal antibodies is DNA. It is generally felt in the industry that the FDA seeks to achieve a DNA level in monoclonal antibody preparations of less than 10 picograms of DNA per dose of monoclonal antibody.

Manufacturers of biological pharmaceuticals such as monoclonal antibodies are required to establish Quality Assurance (QA) procedures to which verify that their products meet standards. In the procedures used to show compliance with the standards, it is necessary that the DNA in a sample be concentrated or solid phased (collected in solid form) from a solution of the biological pharmaceutical. It is known that DNA can be concentrated, solid phased or removed from solution by the use of diethylaminoethyl cellulose (DEAE) filter membranes. A manufacturer's literature (Schleicher & Schuell) indicates that DEAE filters will solid phase more than 90% of *E. coli* DNA from a solution containing 0.2 µg DNA/ml. In a more dilute solution containing 0.001 µg DNA (1 nanogram) more than 80% will be solid phased. The DEAE filters work by binding a protein such as DNA to the filter. However, a major limitation arises in the use of DEAE filters with some monoclonal antibody solutions. For example, it has been found that DNA measurements of monoclonal antibody containing buffer solution having components such as maltose can result in cause false high or low DNA values. In order to assure that the DNA assay values are accurate, these false readings must be eliminated.

Lastly, in addition to viruses and DNA, endotoxins are important contaminating substances in biological pharmaceuticals. While some manufacturers offer column packing materials which are useful in removing endotoxins from protein solutions such as solutions of monoclonal antibodies, such packing materials often result in low product yields after passage of the protein solution through the column. The DEAE filter membranes described above have also been reported to remove endotoxins. However, we have not found the membranes to be effective in removing endotoxins from all sources. In some instances removal is high, whereas in others it is low. This variation is believed to be due to structural variation of the endotoxins themselves in the various samples. The variations in the endotoxins are, in turn, believed dependent on the source of the endotoxin itself and on the chemical treatment it has been subjected to. Having done a careful study of the extant art, we have developed a single filtration device capable of removing virus, DNA and at least some endotoxins to lower levels than previously achieved.

SUMMARY OF THE INVENTION

A single filtration device containing DEAE coated filter membranes and absolute pore filters is provided in which the membranes and absolute pore filters are present in two sections of the filter device. The first section of the device is the DNA filter section comprising a first 0.2 micron filter, a first DEAE filter, a second DEAE filter and a second 0.2 micron filter. The second section is the virus filter section comprising a first 0.1 micron filter, a second 0.1 micron filter, a first 0.04 micron filter and a second 0.04 micron filter. The filter sections can be housed in a single filter device or, alternatively, the sections can be housed in separate housings provided that in use the housing containing the DNA filter section precedes the housing containing the virus filter section and that the two are connected. In order to achieve higher levels of filtration than that afforded by a single device, multiple devices can be combined in series. The device may be used on a large scale at the point of manufacturing or packaging a pharmaceutical solution, or it can be used on a small scale at the point of administration to a patient. In either case, the DNA and viruses are removed by passing the pharmaceutical solution through the DNA and virus filters by the use of either pressure to push the solution through the filter elements, as when administering to a patient, or vacuum to pull the solution through the filter elements as in some manufacturing procedures.

The apparatus embodying the invention will remove viruses, as modeled by type-C Xenotropic retrovirus, with an efficiency of at least $4.6 \times 10^5$ or approximately 99.995%, or $3 \times 10^{10}$ bacteriophage (99.99999997%); remove DNA from levels of 10 μg/sample to levels below 10 picograms per 500 mg sample of monoclonal antibody and preferably below 1 picogram per sample (100 ml of water or solution); and will remove at least 97% of some bacterial endotoxins. Further, these filters units absorb less than 10% of the pharmaceutical or biological pharmaceutical, and most often 6% or less of such pharmaceuticals, particularly monoclonal antibodies and bovine serum albumin.

In an alternative embodiment of the invention, the DEAE filter membranes are replaced by absolute pore filters which have been coated with DEAE, QAE (quaternary aminoethyl salts), QAM (quaternary aminoethyl salts) or other like quaternary salts. For example, the first and second DEAE filters can be replaced by 0.04 micron filters coated with QAE or QAM.

In an alternative embodiment of the invention, an improved apparatus wherein DEAE functional groups, QAE, QAM or other quaternary amine functional groups are bonded directly to one or more of the 0.2, 0.1 and 0.04 micron absolute pore size filters, said functionalized absolute pore filters thereby replacing the DEAE cellulose filters.

BRIEF DESCRIPTION OF THE DRAWINGS

FIG. 1 is a perspective view of single unit of filter apparatus embodying the invention;

FIG. 2 is an exploded view of the apparatus shown in FIG. 1;

DETAILED DESCRIPTION OF THE INVENTION

Figure 3:
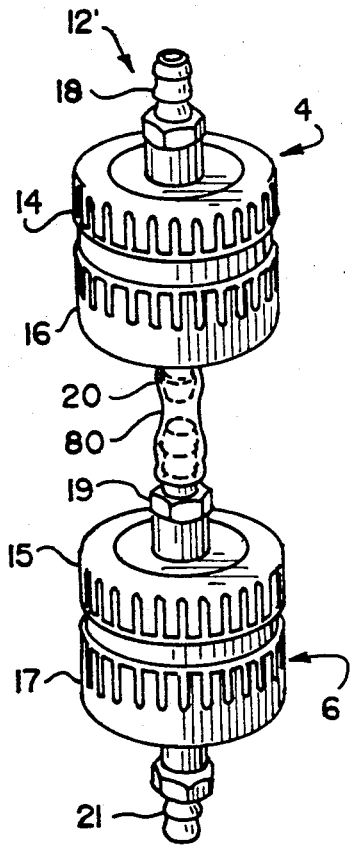
FIG. 3 is a perspective view of a multiple unit filter apparatus embodying the invention.

Referring to FIG. 1, the invention is a filter device 12 comprising a two-piece filter housing part having a top part 14 with inlet port 18, a base part 16 with outlet port 20 and a series of internal elements (not shown) with said top part and base part being joined together in a leakproof manner; for example, by screwing the two parts together, by ball and socket attachment or other such means.

FIG. 2 is an exploded view of apparatus of the invention. The apparatus comprises the visible external members 14, 16, 18 and 20 as described above and internal elements, said internal elements being a first flat filter support 24 having a plurality of channels 26 extending through the thickness of the support; a first sealing member 28 extending a lateral distance inward from the inner wall of the filter housing; a first filter section 30 having filter elements 32, 34, 36 and 38 in sequential facial contact from one to the other throughout; a filter support 40 with a flat top face 42 in contact with the bottom face of filter element 38, a plurality of channels 26 extending through the thickness of the support and a plurality of rigid legs 44 at the outer edge of the bottom face of said support; a second flat filter support 46 having a plurality of channels 26 extending through the thickness of the support and whose top face 48 is in contact with legs 44; a second sealing member 50; a second filter section 60 having filter elements 62, 64, 66 and 68 in sequential facial contact from one to the other throughout; a third flat filter support 70 having a plurality of channels 26 extending through the thickness of said support; and wherein the top to bottom face contact of the element is 28 to 24, 32 to 28, 34 to 32, 36 to 34, 38 to 36, 40 to 38, 50 to 46, 62 to 50, 64 to 62, 66 to 64, 80 to 66 and 70 to 68; and the top of face of element 24 is supported by the interior of top housing 14 and the bottom fact of element 72 is supported by the interior of housing 16; and wherein sealing said interior elements by joining said top and base housing causes a pressure to be exerted on said sealing members 28 and 50 causing said sealing members to seal to the walls of said housing thereby preventing flow around filter sections 30 and 60, and forcing said flow to occur only through said filter sections.

Referring to FIG. 3, a second embodiment of the invention is a two section filter device 12 having a first DNA removal filter unit 4 and a second virus removal unit 6 joined by a connecting means 80.

Figure 4:
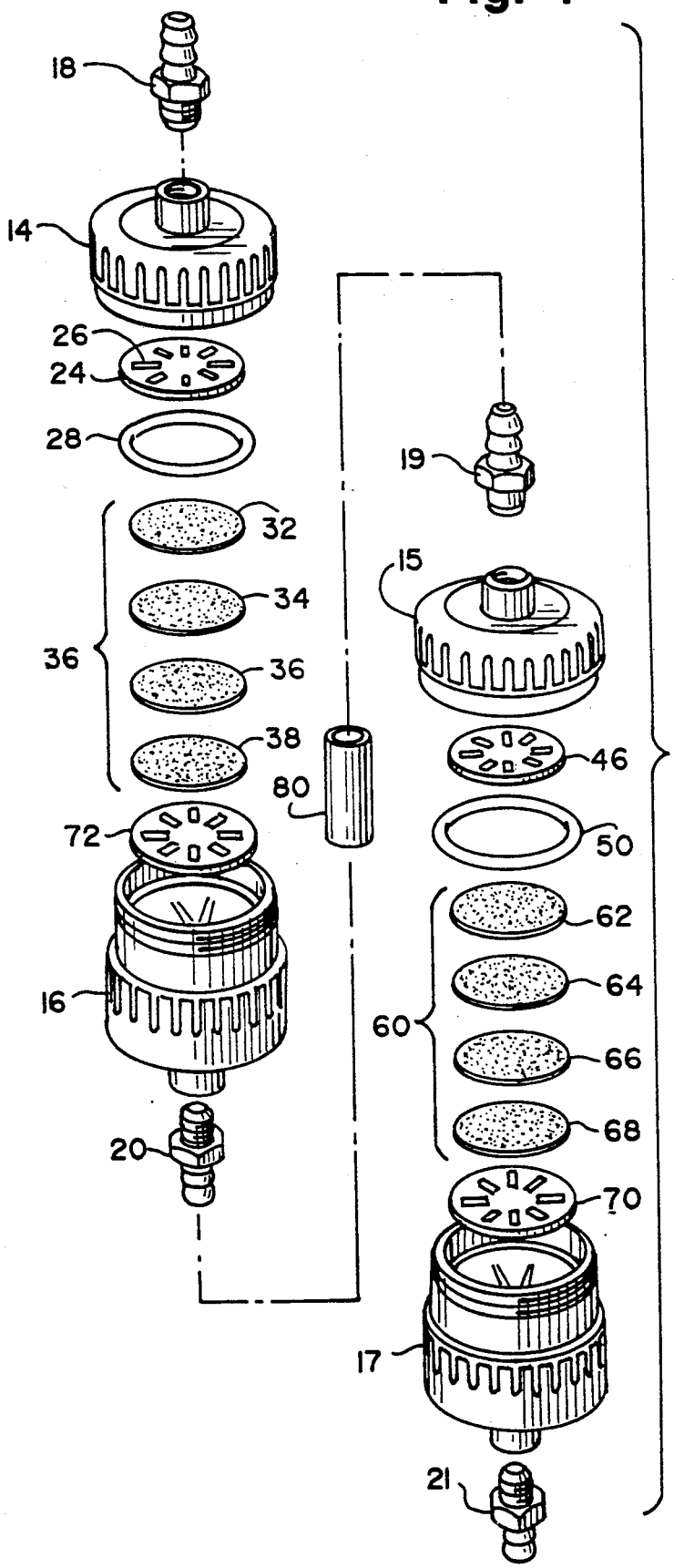
FIG. 4 is an exploded view of the apparatus shown in FIG. 3.

FIG. 4 is an exploded view of the two unit filter device as shown in FIG. 3 comprising a first DNA removal filter unit having a top filter housing part 14 with inlet port 18 and a base filter housing part 16 with outlet port 20, and internal members flush to the interior walls and sequentially in facial contact with each other; said internal members being a first flat filter support 24 having a plurality of channels 26 extending through the thickness of the support; a sealing member 28 in contact with the inner side walls of said housing and extending a lateral distance inward from the inner wall; a DNA filter section 30 having filter elements 32, 34, 36 and 38; a second flat filter support 72 having a plurality of channels extending through the thickness of the support; and a second virus removal filter unit 6 having a top filter housing part 15 with inlet port 19 and a base filter housing part 17 with outlet port 21 and internal members which are sequentially in facial contact with each other;

said internal members being a first flat filter support 46 having a plurality of channels extending through the thickness of said support; a first sealing member 50 in contact with the inner side walls of said housing and extending a lateral distance inward from said inner wall; a virus filter section 60 having filter elements 62, 64, 66 and 68; and a filter support member 62 having a plurality of channels 26 extending through the thickness of said support; and a connecting member 80 joining said DNA filter unit 4 and said virus removal filter unit 6 by connecting outlet port 20 and inlet port 19; wherein the top to bottom face contact of the elements is 28 to 24, 32 to 28, 34 to 32, 36 to 34, 38 to 36, 72 to 38, 50 to 46, 62 to 50, 64 to 62, 66 to 64, 68 to 66, and 70 to 68; and top fact of elements 24 and 46 is supported by the interior of their respective housings 14 and 15 and the bottom face of elements 70 and 72 is supported by the interior of their respective housings 16 and 17; and whereby enclosing said interior elements by joining respective top and base housings parts causes a pressure to be exerted on said sealing members thereby preventing flow around filter section 30 and 60, and forcing said flow to occur only through said respective filter sections; and said first DNA removal filter part and said second virus removal filter part being joined by connecting means 80 attached to parts 19 and 20.

The filter units of as described above can be in any size and shape -round, square, rectangular- possible, subject only to limitation of the availability of size and shape of the filter material for filter sections 30 and 60. The filter units can be sized to handle commercially useful quantities of water for use in the manufacture or preparation of buffer solution, pharmaceuticals, and pharmaceuticals solutions and the like. The filter can be used at any point in a manufacturing processes where a new aqueous material is added and is especially useful in removing DNA, viruses and endotoxins in the packaging step at the end of the manufacturing process. In addition, the filter system of the present invention can be used in conjunction with a device for administering a physiological or a pharmaceutical solution to a patient; for example, the filter system can be built into or placed into a hypodermic syringe. In all instances of use, the solution being filtered passes through the DNA removal filter section and then passes through the virus removal filter section.

The filter elements of the filter apparatus described above are a combination of diethylaminoethyl cellulose and absolute pore filters. These filters, when used in the apparatus of this invention, will remove on 0.1 micron type-C retrovirus with an efficiency of $4.6 \times 10^5$ or higher, remove DNA to level of 10 micrograms/ml to levels below 1 picogram/ml and will remove about 97% of some bacterial endotoxins. In addition, the filter elements of the present invention absorb 6% or less of proteins from the solution under treatment: for example, monoclonal antibody or bovine serum albumin solution. In the preferred embodiment of the invention elements 32 and 38 are 0.2 micron absolute pore filters; elements 34 and 36 are DEAE coated filters such as, for example, Schleicher & Schuell's NA45 filters; elements 62 and 64 are 0.1 micron absolute filters; and elements 66 and 68 are 0.04 micron absolute pore filters.

In the preferred embodiment of the invention, infectious virus particles of about 0.108 micron size can be removed with an efficiency of at least 99.99% per passage through the filtration apparatus. Higher efficiencies can be obtained by using two or more of the filter apparati in series.

The preferred filter apparatus of the invention provides for a synergistic effect upon use of the filter elements as specified. The smallest absolute pore filter of the invention is 0.04 microns. Manufacturer's literature for the DEAE filters state that the pore size is 0.45 microns. However, as stated above and shown in the examples below, virus as small as 0.018 micron (the minimum virus particle size) can be removed. While the exact nature of the synergistic effect is not known, complete removal of virus 55% smaller than the smallest pore size filter element was not anticipated.

In a process utilizing the device of this invention, the water, aqueous buffer solutions and pharmaceutical solutions, including biological pharmaceutical solutions, have a pH in the range of 3 to 9. Further, these solutions have a specific salt content of less than 0.5 Molar, said specific salts being one or more selected from the group consisting of the lithium, sodium, potassium or ammonium salts of the phosphate, chloride, bromide, iodide, sulfate and acetate anions. When utilizing the device of this invention, solutions are first passed through the DNA removal section prior to passage through the virus removal section.

The following examples are given to illustrate the utility of the present invention and are not to be construed as limiting the scope of the invention.

EXAMPLE 1

Virus Removal

The internal elements of the filter unit of the invention were assembled using eight filter element in the sequence 0.2 micron, DEAE, DEAE, 0.2 micron, 0.1 micron, 0.1 micron, 0.04 micron and 0.04 micron. The 0.2, 0.1 and 0.04 micron elements were absolute pore filters, and the DEAE elements were NA 45 filters (Schleicher & Schuell). The units were sealed in autoclavable syringes and were autoclaved or gas sterilized using standard procedures. The sterilized syringes containing the filter elements were sent to Microbiological Associates, Inc., Life Sciences Center, 9900 Blackwell Road, Rockville, Md. 20850 for evaluation with monoclonal antibody solutions spiked with mouse xenotropic retrovirus of similar size to type C retrovirus (0.1 micron v 0.104 micron respectively). Each syringe filter device was evaluated against one sample of retrovirus spiked monoclonal antibody. By S+L- assay, the samples contained $4.37 \times 10^5$, $5.6 \times 10^5$ and $4.1 \times 10^5$ FFU/ml.

$$[FFU/ml = (mean\ number\ of\ foci/dish \times volume^1 dish^x dilution^1]$$

After passage of the test samples through the syringe filter units, the filtrates were re-analyzed in triplicate for retrovirus. No retrovirus found in any of the three monoclonal antibody filtrates. Antibody recovery was greater than 90%.

EXAMPLE 2

Removal of Bacteriophage By DNA/Virus Removal Filters

The maximum concentration of xenotropic retrovirus attainable is about $10^6$ FFU/ml. In order to validate the DNA/Virus removal filters of this invention for higher virus particle removal efficiencies, bacteriophage T4

(approximately 0.1 micron) was chosen as a second model virus. The assay for bacteriophage T4 concentration was the formation of plaques (PFU) on a lawn of *Escherichia coli* B (ATCC 11303). The bacteriophage T4 was grown to maximum concentration ($9.9 \times 10^{10}$ PFU/ml) and the undiluted bacteriophage solution was divided into three aliquots. Each aliquot was filtered through a separate DNA/Virus removal filter device. The concentration of bacteriophage T4 in the filtrate was assayed by dilution and plating on dishes of *E. coli*. None of the three filtrates contained viable virus. The assay has an uncertainty of 3.3 FFU. These results indicate that the DNA/Virus removal filter device of the present invention is capable of reducing the concentration of an 0.1 micron bacteriophage by at least $3.0 \times 10^{10}$ fold (99.99999997%). Similar results should be obtainable with viruses of similar size, approximately 0.1 micron, such as type C retrovirus. Type C retrovirus has been found to be a contaminant in the conditioned raw material for monoclonal antibody pharmaceutical. To the inventors' knowledge, no single pass through any filter as previously achieved this level of virus removal. Using the filter device of the present invention should reduce the concentration of type C retrovirus in the conditioned raw material by at least $3 \times 10^{10}$ fold. Thus, solutions containing nominal virus counts on the order of $10^7$ should be able to be filtered to an undetectable virus level with a 1000 fold safety margin. In those cases where the virus load of a solution is higher, over $10^7$, the solution can be filtered two or more times to obtain a solution having an undetectable virus level. Using two of the filter devices of the present invention in series would allow the removal of approximately $10^{17}-10^{18}$ virus particles per ml $[(3 \times 10^{10}) \times (3 \times 10^{10})/1000 = 9 \times 10^{17}]$.

EXAMPLE 3

DNA Removal From Spiked Antibody Solutions

Monoclonal antibody solutions containing 400 mg of antibody each and DNA were filtered through the DNA/virus removal filter unit of the invention. DNA analysis before and after filtration showed 727 pg and 442 pg of DNA per sample before filtration; and 5pg and 1pg DNA, respectively, after filtration (99.3% and 99.8% removal).

EXAMPLE 4

DNA Removal From Commercial Antibody Solutions

Analysis of commercial monoclonal antibody solutions indicated that there is significant DNA contamination. The analysis was performed using an assay kit from FMC Bio Products, Rockland, Me. (FMC assay) for the detection of DNA solid-phased on Nylon 66 membranes. Five lots of DNA containing monoclonal antibody solution were analyzed for DNA before and after filtration through a filter device of the invention: All filtered solutions had less than 10 picograms of DNA per dose of antibody and two of the five showed less than 1 picogram per dose. The results are shown in Table 1.

TABLE 1

SUMMARY of DNA REMOVAL from antibody products

| Product No. | Mean DNA Before Filtration | | Concentration After Filtration |
|---|---|---|---|
| | pg DNA/mg Mab: | pg DNA/dose | pg DNA/dose |
| 1 | 0.65 | 260 | 2.6 |
| 2 | 0.30 | 120 | 0.4 |
| 3 | 0.34 | 3.4 | 2.6 |
| 4 | 0.13 | 1.3 | 3.1 |
| 5 | 0.14 | 140 | 0 |

EXAMPLE 5

DNA Removal Validation

In order to validate DNA removal for commercial purposes, the DNA/Virus removal filters were challenged with 500 mg samples of a pharmaceutical grade monoclonal antibody (B1) in buffer spiked with 100 micrograms of hybridoma produced DNA. The DNA used in the validation was purified from the same cell culture medium used to produce monoclonal antibodies and was as similar as possible to the DNA actually encounted in the production of the antibody. Three antibody solutions were spiked with the DNA. Two unspiked antibody solutions, two buffer (only) solutions without DNA and two buffer (only) solutions spiked with 100 micrograms of DNA were used as controls. The actual level of DNA in the spiked solutions was determined by means of a fluorescent DNA assay technique. The spiked antibody solutions were found to have actual DNA levels of 81, 92 and 74 micrograms per sample. The spiked buffer solutions were found to have actual DNA levels of 89 and 96 micrograms per sample. All solutions samples were equal volume.

Each of the test solutions (9 solutions total) was filter through a separate 25 mm DNA/Virus removal filter device. The residual DNA in each filtrate was concentrated, solid phased and quantified in duplicate using standard FMC DNA assay techniques. The quantity of DNA in each assay was determined from a standard curve of purified hybridoma DNA run in the same assay. For the standard curve, the color intensities of the sample bands, measured by the instrument's reflection densitometer, are measured as peak heights in centimeters. The standard curve data is linearly transformed by a log-logit transformation where the peak heights are converted to a logit (relative to a standard that will give maximum color development and a blank) versus the log of the picograms of DNA standard added. Test samples were then interpolated from the standard curve of DNA to color intensity. The results are given in Table 2 and indicate that a single pass through the DNA/Virus removal filter is capable of reducing the DNA levels by about $10^7$ fold to approximately 10 picograms DNA per 500 mg of monoclonal antibody (mean = 12.3 pg DNA/500 mg antibody). The mean value for an equal volume of unspiked buffer (only) is 6.2 pg. Therefore, the mean net DNA detected in the filtered, spiked antibody solution is 6.1 pg DNA/500 mg antibody.

TABLE 2

| Sample | DNA Spike | DNA Detected in sample after DNA spiking | % Recovery of protein concentration (Lowry) | Mean total DNA detected Mean after filtration |
|---|---|---|---|---|
| B1 500 mg | 100 ug | 81 ug | 98.9% | 16.5 pg |

TABLE 2-continued

| Sample | DNA Spike | DNA Detected in sample after DNA spiking | % Recovery of protein concentration (Lowry) | Mean total DNA detected after filtration | Mean |
|---|---|---|---|---|---|
| B1 500 mg | 100 ug | 92 ug | 98.0% | 8.6 pg | 12.3 pg |
| B1 500 mg | 100 ug | 74 ug | 96.7% | 11.7 pg | |
| B1 500 mg | 0 | 0 | 96.3% | 3.3 pg | |
| B1 500 mg | 0 | 0 | 92.8% | 3.2 pg | 3.2 pg |
| Buffer | 100 ug | 89 ug | N/A | 16.9 pg | |
| Buffer | 100 ug | 96 ug | N/A | 3.3 pg | 10.1 pg |
| Buffer | 0 | 0 | N/A | 9.8 pg | |
| Buffer | 0 | 0 | N/A | 2.6 pg | 6.2 pg |

*total DNA in 500 mg sample of monoclonal antibody (mean observation of samples assayed in duplicate)

EXAMPLE 6
Endotoxin Removal

A 100 ml solution of 50 mg/ml bovine serum albumin in 10% maltose-phosphate buffers solution contaminated with DNA and a endotoxin was filtered through a 47 mm DNA/virus removal filtration device. The starting solution contained 248 pg/ml DNA and 1966 endotoxin units ml (EU/ml).

First, middle and end 20 ml portions of the filtrate were collected and analyzed. No DNA was detected in any analyzed portion of filtrate. Endotoxin levels were: first=30.72 EU/ml, middle=30.72 EU/ml and last=61.44 EU/ml. Endotoxin removal in the end sample was 96 9%. Solution recovery was 95% (95 ml) with no change in protein concentration.

We claim:

1. A process for the removal of DNA, endotoxins and viruses from aqueous buffer solutions, aqueous pharmaceutical solutions and aqueous biological pharmaceutical solutions comprising, passing one of said aqueous buffer solutions, aqueous pharmaceutical solutions and aqueous biological pharmaceutical solutions through a first DNA filter section and a second virus filter section, wherein said DNA, viruses and endotoxins are substantially removed; and collecting said aqueous buffer solutions, aqueous pharmaceutical solutions or aqueous biological pharmaceutical solutions; said first DNA filter having:
   (i) a first absolute pore filter,
   (ii) a first and second filter selected from one of (a) a DEAE cellulose filter membrane and (b) an absolute pore filter coated with at least one of DEAE cellulose, quaternary aminoethyl salts and quaternary aminomethyl salts, and
   (iii) a second absolute pore filter; and said second virus filter section having absolute pore filters of smaller pore diameter than the absolute pore filters in the DNA filter section.

2. A process in accordance with claim 1 wherein the yield of pharmaceuticals, or biological pharmaceuticals in the filtered solutions is 90% or higher compared to the starting solution.

3. A process in accordance with claim 1 wherein the virus removal is 99.9999997% or higher when the virus is 0.100 microns or larger, and the yield of pharmaceutical or biological pharmaceutical in the filtered solution of same is 90% or higher compared to the starting solution.

4. A process in accordance with claim 1 wherein said DNA in the filtered solutions is less than 10 picograms per 100 ml of solution.

5. A process in accordance with claim 1 wherein the aqueous buffer solutions, aqueous pharmaceutical solutions and aqueous biological pharmaceutical solutions have a pH in the range of 3 to 9.

6. A process in accordance with claim 1 wherein the aqueous buffer solutions, aqueous pharmaceutical solutions and aqueous biological pharmaceutical solutions each have a specific salt content of less than 0.5 Molar, said specific salt being at least one selected from the group consisting of the lithium, sodium, potassium and ammonium salts of the phosphate, chloride, bromide, iodide, sulfate and acetate anions.

7. A process in accordance with claim 1 wherein said DNA in the filtered solutions is less than 1 picogram per 100 ml of solution.

8. A process for the removal of DNA and viruses from aqueous pharmaceutical solutions and aqueous biological pharmaceutical solutions, comprising passing either one of the solutions through a first DNA filter section and a second virus filter section to obtain a filtered aqueous pharmaceutical solution or a filtered aqueous biological pharmaceutical solution having substantially reduced DNA and virus levels, said solutions passing through:
   (a) a first DNA filter section comprising a first 0.2 micron absolute pore filter, a first diethylaminoethyl cellulose filter, a second diethylaminoethyl cellulose filter and a second 0.2 micron absolute pore filter, and
   (b) a second virus filter section comprising a first 0.1 micron absolute pore filter, a second 0.1 micron absolute pore filter, a first 0.04 micron absolute pore filter and a second 0.04 micron absolute pore filter; and collecting the filtered solutions.

9. A process in accordance with claim 8 wherein the yield of the pharmaceutical or biological pharmaceutical, in the filtered solution is 90% or higher.

10. A process in accordance with claim 8 wherein the virus removal is 99.99999997% or when the virus is 0.100 microns or larger, and the yield of the pharmaceutical or biological pharmaceutical in the filtered solution is 90% or higher.

11. A process in accordance with claim 8 wherein the DNA in the filtered pharmaceutical or biological pharmaceutical solution is reduced to less than 10 picograms per 100 ml of solution.

12. A process in accordance with claim 8 wherein the pharmaceutical solution or biological solution has a pH in the range of 6 to 8.

13. A process in accordance with claim 8 wherein the pharmaceutical or biological pharmaceutical has a specific salt content, excluding salts of pharmaceuticals or biological pharmaceuticals, of less than 0.5 Molar, said specific salts being at least one selected from the group consisting the lithium, sodium, potassium and ammonium salts of the phosphate, chloride, bromide, iodide, sulfate and acetate anions.

14. A process in accordance with claim 8 wherein the DNA in the filtered pharmaceutical or biological pharmaceutical solution is reduced to less than 1 picogram per 100 ml of solution.

15. A process in accordance with claim 1 or 8 wherein said aqueous buffer solutions, aqueous pharmaceutical solutions and aqueous biological pharmaceutical solutions are passed through said DNA filter section and said virus filter section by a vacuum means or a pressure means.

16. An improved apparatus for the removal of DNA, endotoxins and viruses from aqueous buffer solutions, aqueous pharmaceutical solutions and aqueous biological pharmaceutical solutions, said apparatus having a housing with suitable inlet/outlet means internal gaskets and filter supports, and internal filters wherein the improvement comprises a first DNA filter section having, from inflow to outflow, a first 0.2 micron filter, a first diethylaminoethyl cellulose filter, a second diethylaminoethyl cellulose filter and a second 0.2 micron filter, the filters having face-to-face contact; and a second virus filter section having, from inflow to outflow, a first 0.1 micron filter, a second 0.1 micron filter, a first 0.04 micron filter and a second 0.04 micron filter, said filters having face-to-face contact.

17. An improved apparatus in accordance with claim 16 wherein said 0.2, 0.1 and 0.04 filters are absolute pore filters.

18. The improved apparatus in accordance with claim 16 wherein said apparatus is capable of removing DNA to a level of less than 10 picograms per 100 ml of solution.

19. The improved apparatus of claim 16 wherein said apparatus is capable of removing 99.9999997% of virus when the virus is 0.100 microns or larger.

20. The improved apparatus of claim 16 wherein the apparatus gives a yield of pharmaceutical or biological pharmaceutical in the filtered solution of 90% or higher compared to the unfiltered solution.

21. The improved apparatus of claim 16 where the solution to be filtered is passed through said apparatus by pressure or vacuum means.

22. The improved apparatus of claim 16 wherein said apparatus is a means of administration of said aqueous buffer solution, aqueous pharmaceutical solution or aqueous biological pharmaceutical solution to a patient which means contains said DNA and virus filter sections.

23. The improved apparatus of claim 16 wherein said apparatus is a syringe filtration device containing said DNA and virus removal filters.

24. The improved apparatus in accordance with claim 14, wherein said apparatus is capable of removing DNA to a level of less than 1 picogram per ml of solution.

25. An improved apparatus for the removal of DNA, endotoxins and viruses from aqueous buffer solutions, aqueous pharmaceutical solutions and aqueous biological pharmaceutical solutions, said apparatus having a housing with suitable inlet/outlet means, internal gaskets and filter supports, and internal filters wherein the improvement comprises a first DNA filter section having, from inflow to outflow, a first 0.2 micron filter, a second 0.2 micron filter, the filters having face-to-face contact; and a second virus filter section having, from inflow to outflow, a first 0.1 micron filter, a second 0.1 micron filter, a first 0.04 micron filter and a second 0.04 micron filter, said filters having face-to-face contact; wherein at least one of the absolute pore filters is coated with at least one of the group consisting of DEAE, QAE, QAM and other quaternary ammonium salts.

26. An improved apparatus for the removal of DNA, endotoxins and viruses from aqueous buffer solutions, aqueous pharmaceutical solutions and aqueous biological pharmaceutical solutions, said apparatus having a housing with suitable inlet/outlet means, internal gaskets and filter supports, and internal filters wherein the improvement comprises a first DNA filter section having, from inflow to outflow, a first 0.2 micron filter, first and second absolute pore filters coated with at least one selected from the group consisting of DEAE cellulose, QAE, QAM and other quaternary ammonium salts, a second 0.2 micron filter, the filters having face-to-face contact; and a second virus filter section having, from inflow to outflow, a first 0.1 micron filter, a second 0.1 micron filter, a first 0.04 micron filter and a second 0.04 micron filter, said filters having face-to-face contact.

* * * * *

UNITED STATES PATENT AND TRADEMARK OFFICE
CERTIFICATE OF CORRECTION

PATENT NO.  : 5,076,933

DATED       : December 31, 1991

INVENTOR(S) : Stephan D. Glenn, Gregory Butchko, Edward O'Connell and Paulette Smariga It is certified that error appears in the above-identified patent and that said Letters Patent is hereby corrected as shown below:

Column 3, line 48, cancel "aminoethyl" and insert --aminomethyl--.

Column 6, lines 3-13, delete "The preferred filter apparatus of the invention provides for a synergistic effect upon use of the filter elements as specified. The smallest absolute pore filter of the invention is 0.04 microns. Manufacturer's literature for the DEAE filters state that the pore size is 0.45 microns. However, as stated above and shown in the examples below, virus as small as 0.018 micron (the minimum virus particle size) can be removed. While the exact nature of the synergistic effect is not known complete removal of virus 55% smaller than the smallest pore size filter element was not anticipated.

Column 6, line 53, cancel "volume disk" and insert --volume/disk--.

Column 9, line 29, cancel "969%" and insert --96.9%--.

Column 10, line 52, after "or" insert --higher--.

UNITED STATES PATENT AND TRADEMARK OFFICE
CERTIFICATE OF CORRECTION

PATENT NO. : 5,076,933
DATED : December 31, 1991
INVENTOR(S) : Stephan D. Glenn, et al It is certified that error appears in the above-indentified patent and that said Letters Patent is hereby corrected as shown below:

Column 10, line 61, after "biological" insert --pharmaceutical--.

Signed and Sealed this

Eighth Day of June, 1993

Attest:

MICHAEL K. KIRK

Attesting Officer     Acting Commissioner of Patents and Trademarks